(12) United States Patent
Wu et al.

(10) Patent No.: US 12,329,985 B2
(45) Date of Patent: Jun. 17, 2025

(54) METHOD AND APPARATUS FOR ADJUSTING DOSE RATES, COMPUTER DEVICE, AND STORAGE MEDIUM

(71) Applicants: OUR UNITED CORPORATION, Xi'an (CN); SHENZHEN OUR NEW MEDICAL TECHNOLOGIES DEVELOPMENT CO., LTD., Shenzhen (CN)

(72) Inventors: Yue Wu, Xi'an (CN); Hong Cheng, Xi'an (CN)

(73) Assignees: OUR UNITED CORPORATED, Xi'an (CN); SHENZHEN OUR NEW MEDICAL TECHNOLOGIES DEVELOPMENT CO., LTD., Shenzhen (CN)

( * ) Notice: Subject to any disclaimer, the term of this patent is extended or adjusted under 35 U.S.C. 154(b) by 191 days.

(21) Appl. No.: 18/174,430

(22) Filed: Feb. 24, 2023

(65) Prior Publication Data
US 2023/0241412 A1    Aug. 3, 2023

(30) Foreign Application Priority Data

Dec. 27, 2021    (CN) .......................... 202111615191.9

(51) Int. Cl.
*A61N 5/10*    (2006.01)
(52) U.S. Cl.
CPC ........... *A61N 5/103* (2013.01); *A61N 5/1071* (2013.01)
(58) Field of Classification Search
CPC .... A61N 5/103; A61N 5/1071; A61N 5/1067; A61N 5/1047
See application file for complete search history.

(56) References Cited

U.S. PATENT DOCUMENTS

2015/0071414 A1*   3/2015   Oda ........................ A61B 6/548
                                                                 378/207
2016/0339271 A1    11/2016   Bach et al.
(Continued)

FOREIGN PATENT DOCUMENTS

| CN | 101797423 A | 8/2010 |
|---|---|---|
| CN | 108744308 A | 11/2018 |

(Continued)

OTHER PUBLICATIONS

China National Intellectual Property Administration, First Office Action in Chinese Patent Application No. 202111615191.9 issued on Jul. 3, 2024, which is a foreign counterpart application corresponding to this U.S. Patent Application, to which this application claims priority.

*Primary Examiner* — Dani Fox
*Assistant Examiner* — Mamadou Faye
(74) *Attorney, Agent, or Firm* — Kolitch Romano Dascenzo Gates LLC

(57) ABSTRACT

Provided are a method and apparatus for adjusting dose rates, a computer device, and a storage medium. In the method, an output pulse frequency is determined based on a current actual dose, a current target dose, and a current pulse frequency, and then a dose rate of a radiation beam emitted by radiation source equipment is updated based on the output pulse frequency. The current pulse frequency is indicative of the dose rate of the radiation beam emitted by the radiation source equipment, the current actual dose is an actually received dose of the radiation beam for a tumor target region, and the current target dose is an expected dose of the radiation beam for the tumor target region.

13 Claims, 4 Drawing Sheets

```
┌─────────────────────────────────────────────────────┐  ─ S102-1
│ Calculating a dose difference value based on the    │
│ current actual dose and the current target dose     │
└─────────────────────────────────────────────────────┘
                            │
                            ▼
┌─────────────────────────────────────────────────────┐  ─ S102-2
│ Determining a pulse frequency compensation value    │
│ based on the dose difference value and the current  │
│ pulse frequency                                     │
└─────────────────────────────────────────────────────┘
                            │
                            ▼
┌─────────────────────────────────────────────────────┐  ─ S102-3
│ Acquiring the output pulse frequency by adjusting,  │
│ based on the pulse frequency compensation value,    │
│ the current pulse frequency                         │
└─────────────────────────────────────────────────────┘
```

(56) References Cited

U.S. PATENT DOCUMENTS

2018/0020535 A1\* 1/2018 Cooley ................ A61N 5/1037
2019/0060669 A1 2/2019 Stahl et al.
2019/0255362 A1 8/2019 Voronenko et al.

FOREIGN PATENT DOCUMENTS

| CN | 109157763 A | 1/2019 |
| CN | 111954496 A | 11/2020 |
| EP | 2493567 A1 | 9/2012 |

\* cited by examiner

METHOD AND APPARATUS FOR ADJUSTING DOSE RATES, COMPUTER DEVICE, AND STORAGE MEDIUM

CROSS-REFERENCE TO RELATED APPLICATION

This application is based on and claims priority to Chinese Patent Application No. 202111615191.9, filed on Dec. 27, 2021 and entitled "DOSE RATE INTENSITY MODULATION METHOD AND DEVICE, COMPUTER EQUIPMENT AND STORAGE MEDIUM", the disclosure of which is herein incorporated by reference in its entirety.

TECHNICAL FIELD

The present disclosure relates to a method and apparatus for adjusting dose rates, a computer device, and a storage medium.

BACKGROUND OF THE INVENTION

The volumetric modulated arc therapy (VMAT) is a common arc therapy technology. In the VMAT, radiation source equipment and a movement of a gantry are combined to change a dose rate of a radiation beam emitted by the radiation source equipment and a radiation field shape when the gantry rotates around a patient, and to continuously irradiate a tumor target region. In the irradiation process, irradiation doses to the tumor target region at all angles are integrated and superimposed to form a dose distribution with a great conformance, such that radiation doses of organs around the tumor target region are less, and the radiation dose of the tumor target region is great, thereby reducing related side effects caused by the arc therapy.

SUMMARY OF THE INVENTION

Embodiments of the present disclosure provide a method and apparatus for adjusting dose rates, a computer device, and a storage medium.

In some embodiments of the present disclosure, a method for adjusting dose rates is provided. The method includes:
acquiring a current actual dose, a current target dose, and a current pulse frequency, wherein the current pulse frequency is indicative of a dose rate of a radiation beam emitted by radiation source equipment, the current actual dose is an actually received dose of the radiation beam actually for a tumor target region, and the current target dose is an expected dose of the radiation beam for the tumor target region;
determining an output pulse frequency based on the current actual dose, the current target dose, and the current pulse frequency; and
updating, based on the output pulse frequency, the dose rate of the radiation beam emitted by the radiation source equipment.

In some embodiments, determining the output pulse frequency based on the current actual dose, the current target dose, and the current pulse frequency includes:
calculating a dose difference value based on the current actual dose and the current target dose, wherein the dose difference value is an absolute value of a difference value between the current actual dose and the current target dose;
determining a pulse frequency compensation value based on the dose difference value and the current pulse frequency; and
acquiring the output pulse frequency by adjusting, based on the pulse frequency compensation value, the current pulse frequency.

In some embodiments, determining the pulse frequency compensation value based on the dose difference value and the current pulse frequency includes:
determining, in response to the dose difference value being not less than a target threshold, the pulse frequency compensation value based on the dose difference value, a single pulse dose, and the current pulse frequency,
wherein the single pulse dose is a dose of a signal pulse of the radiation beam emitted by the radiation source equipment.

In some embodiments, determining the pulse frequency compensation value based on the dose difference value, the single pulse dose, and the current pulse frequency includes:
determining a reference compensation value based on the dose difference value, the single pulse dose, a first period, and a second period, wherein the reference compensation value is positively correlated with the dose difference value and is negatively correlated with the single pulse dose, the first period, and the second period, the first period is a duration required for each rotation of the radiation source equipment by a target angle, and the second period is a number of rotations of the radiation source equipment between each two adjacent adjustments of the dose rate;
determining a first correction coefficient based on the dose difference value, wherein the first correction coefficient is a value of a piecewise function of the dose difference value, and is positively correlated with the dose difference value;
determining a second correction coefficient based on the reference compensation value, wherein the second correction coefficient is a value of a piecewise function of the reference compensation value, and is negatively correlated with the reference compensation value; and
determining the pulse frequency compensation value based on the first correction coefficient, the second correction coefficient, the current pulse frequency, and the reference compensation value.

In some embodiments, determining the pulse frequency compensation value based on the first correction coefficient, the second correction coefficient, the current pulse frequency, and the reference compensation value includes:
determining a first threshold and a second threshold based on the first correction coefficient, the second correction coefficient, and the current pulse frequency;
determining the first threshold as the pulse frequency compensation value in response to the reference compensation value being less than the first threshold;
determining the reference compensation value as the pulse frequency compensation value in response to the reference compensation value being greater than or equal to the first threshold and being less than or equal to the second threshold; and
determining the second threshold as the pulse frequency compensation value in response to the reference compensation value being greater than the second threshold.

In some embodiments, the method further includes:
performing an output limitation on the output pulse frequency based on third parameters.

In some embodiments, the third parameters include a maximum dose rate of the radiation beam, a pulse frequency conversion coefficient, a pulse frequency tolerance value, and a maximum value of the output pulse frequency, and the pulse frequency conversion coefficient is a parameter based on which a pulse frequency is converted to a rotation speed of the radiation source equipment; and performing the output limitation on the output pulse frequency based on the third parameters includes:

determining, in response to the output pulse frequency being greater than a ratio of the maximum dose rate to the pulse frequency conversion coefficient, a calculation result acquired based on the maximum dose rate of the radiation beam, the pulse frequency conversion coefficient, the pulse frequency tolerance value, and the maximum value of the output pulse frequency as the output pulse frequency.

In some embodiments, in response to the updated dose rate, the actually received dose of the radiation beam for the tumor target region approaches to the expected dose of the radiation beam for the tumor target region.

In some embodiments of the present disclosure, an apparatus for adjusting dose rates is provided. The apparatus includes:

an acquiring module, configured to acquire a current actual dose, a current target dose, and a current pulse frequency, wherein the current pulse frequency is indicative of a dose rate of a radiation beam emitted by radiation source equipment, the current actual dose is an actually received dose of the radiation beam for a tumor target region, and the current target dose is an expected dose of the radiation beam for the tumor target region;

a determining module, configured to determine an output pulse frequency based on the current actual dose, the current target dose, and the current pulse frequency; and an updating module, configured to update, based on the output pulse frequency, the dose rate of the radiation beam emitted by the radiation source equipment.

In some embodiments of the present disclosure, a computer device is provided. The computer device includes a memory, a processor, and radiation source equipment, wherein the memory is configured to store one or more computer programs, and the processor, when loading and running the one or more computer programs, is caused to perform the method according to above embodiments.

In some embodiments of the present disclosure, a computer-readable storage medium is provided. The computer-readable storage medium stores one or more computer programs thereon, wherein the one or more computer programs, when loaded and run by a processor, cause the processor to perform the method according to above embodiments.

In some embodiments of the present disclosure, a computer program product is provided. The computer program product includes instructions, wherein the computer program product, when loaded and run by a computer, causes the computer to perform the method according to above embodiments.

In some embodiments of the present disclosure, a chip is provided. The chip includes at least one of a programmable logic circuit and a program instruction, wherein the chip, when running, is caused to perform the method according to above embodiments.

Figure 1:
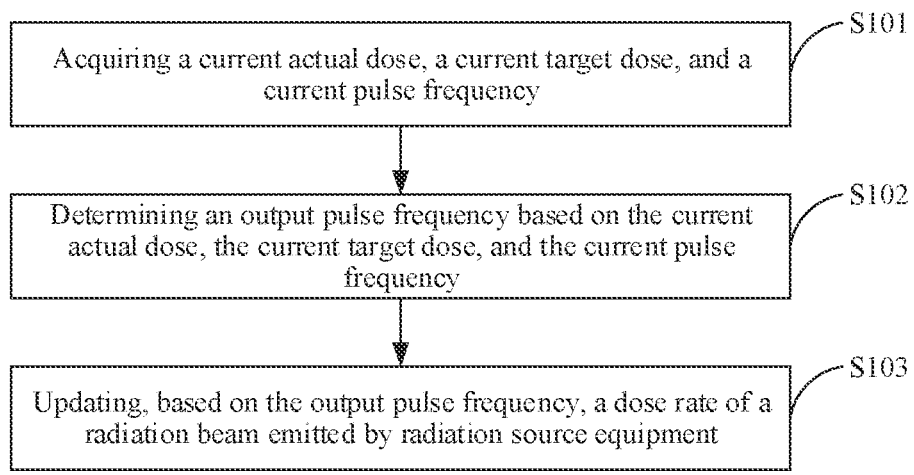
FIG. 1 is a flowchart of a method for adjusting dose rates according to some embodiments of the present disclosure.

Reference numerals: 100—apparatus for adjusting dose rates; 101—acquiring module; 102—determining module; 103—updating module; 200—computer device; 210—memory; 220—processor; 230—radiation source equipment.

DETAILED DESCRIPTION

To make the principles, technical solutions, and advantages of the embodiments of the present disclosure clearer, the technical solutions of the embodiments of the present disclosure are described clearly and completely in conjunction with the accompanying drawings in the embodiments of the present disclosure. Apparently, the described embodiments are only a part of embodiments of the present disclosure, not all embodiments. Generally, assemblies of the embodiments of the present disclosure described and shown in the accompanying drawings are disposed and designed in different configurations.

Therefore, the following detailed descriptions of the embodiments of the present disclosure provided in the accompanying drawings are not intended to limit the scope of protection of the present disclosure, but merely constructed as the selected embodiments of the present disclosure. All other embodiments achieved by persons skilled in the art based on the embodiments of the present disclosure without creative work shall fall within the scope of protection the present disclosure.

It should be noted that similar labels and letters indicate similar items in the following accompanying drawings. Thus, once an item is defined in one accompanying drawing, it is not necessary to further define or explain in subsequent accompanying drawings.

In the description of the present disclosure, directional or positional relationships shown by the terms such as "upper," "lower," "inner," and "outer" are directional or positional relationships based on the accompanying drawings, or directional or positional relationships of the product generally placed in use, which only intend to facilitate description of the present disclosure and simplify the description, but do not indicate or imply that the apparatuses or components must have specific directions, or be constructed or operated in the specific directions, and thus are not limitative of the present disclosure.

The terms "first" and "second" are only for distinguishing description and should not be understood as indicating or implying relative importance. The symbol "I" indicates a "or" relationship of the content before and after it.

It should be noted that the features in the embodiments of the present disclosure can be combined without conflict.

The arc therapy is a technology of a therapy for tumors using high-energy rays generated by radiation source equipment. Arc therapy equipment is equipment that generates radiation using atomic nuclei or artificial devices to treat tumors. For example, cobalt-60 therapy machine is equipment that takes cobalt-60 as a radiation source and uses gamma rays to kill cancer cells to treat tumors. Medical electronic linear accelerator is equipment that uses microwave electric field to linearly accelerate electrons to higher energy and applies it to medical clinic.

Therapy plan design is an important part in arc therapy process, which refers to a whole process of determining the therapy plan. The therapy plan design can be understood as that a computer controlling the arc therapy equipment arranges an appropriate radiation field based on input external contours of a therapy site of a patient, contours of important tissues and organs in the tumor target region, and a density of relevant tissues. The therapy plan design also includes calculation of doses using radiation field baffles or tissue compensators, so as to acquire required dose distribution. A dose detection system is composed of a dose monitoring ionization chamber and a dose detection circuit, and is generally disposed in a radiation head of the arc therapy equipment. The computer acquires the implementation of therapy doses by the dose detection system.

Current arc therapy technologies include three dimensional conformal radiation therapy (3D-CRT), intensity modulated radiation therapy (IMRT), and volumetric modulated arc therapy (VMAT). VMAT has characteristics of greater conformance of dose distribution, more accurate dose, less irradiation dose to the organs around the tumor target region (that is, a dose, irradiated to the organs, of a radiation beam emitted by the radiation source equipment), and great irradiation dose to the tumor target region, and thus an efficiency of the arc therapy is significantly improved, and related side effects are reduced.

At present, VMAT is mainly used for cases of small target region, while huge tumors or systemic niduses need to be treated in several times or stages. In staged VMAT for the tumor target region, a dose rate and radiation field shape of the radiation beam emitted by the radiation source equipment are not changed in each stage of the therapy process. Compared with not-staged VMAT, a gamma pass rate of the case is improved, but a difference value is present between an actual dose acquired by integrating and superimposing the irradiation doses of the radiation beam to the tumor target region in each stage and a target dose required in the therapy plan, such that a therapy effect is poor.

The medical electronic linear accelerator includes a modulator and a microwave system. The modulator is configured to emit a high voltage of a pulse, and the microwave system is configured to emit microwave based on the high voltage, such that a magnetic field is formed based on the microwave. The magnetic field is used to accelerate electrons, and the accelerated electrons are taken as rays in the radiation beam. Modulator pulse loss or microwave system failure (for example, ignition) may occur in the electronic linear accelerator. In this case, the above difference value is further amplified, such that final therapy effect does not meet requirements of the therapy plan.

Therefore, a method for adjusting dose rates is provided in the embodiments of the present disclosure, such that the radiation source equipment is capable of flexibly controlling the dose rate of the radiation beam in the arc therapy process, a deviation between the actual arc therapy effect and the result specified in the therapy plan is reduced, and the therapy effect is improved.

Referring to FIG. 1, FIG. 1 is a flow chart of a method for adjusting dose rates according to some embodiments of the present disclosure. The method is applicable to the radiation source equipment, and is used in staged therapy to the tumor target region. The method includes S101 to S103.

In S101, a current actual dose, a current target dose, and a current pulse frequency are acquired, wherein the current pulse frequency is indicative of a dose rate of a radiation beam emitted by radiation source equipment.

A pulse frequency is indicative of a number of pulses of the radiation beam emitted by the radiation source equipment in unit time, and a dose of the radiation beam corresponding to single pulse (hereinafter short for a single pulse dose) is 0.1 monitor unit/pulse (MU/pulse) generally. In the embodiments of the present disclosure, the pulse frequency is indicative of a dose of the radiation beam emitted by the radiation source equipment in the unit time, that is, the dose rate. It should be understood that the current pulse frequency is indicative of the dose rate of the radiation beam emitted by the radiation source equipment at the current moment.

The current actual dose is an actually received dose of the radiation beam for a tumor target region, for example, an actual result acquired by integrating and superimposing the irradiation dose rates to the tumor target region in the stages in the staged therapy process up to the current moment. The current target dose is an expected dose, specified in the therapy plan, of the radiation beam for the tumor target region, for example, an expected dose by integrating and superimposing the irradiation dose rates received by the tumor target region up to the current moment. The current pulse frequency and the current actual dose are acquired by the dose detection system disposed in the radiation source equipment, and the current target dose is acquired form the therapy plan of the therapy site of the patient.

In S102, an output pulse frequency is determined based on the current actual dose, the current target dose, and the current pulse frequency.

In the embodiments of the present disclosure, the current actual dose is indicative of an actual arc therapy effect, and the current target dose is indicative of an arc therapy result specific in the therapy plan. The pulse frequency of the radiation beam emitted by the radiation source equipment, that is, the output pulse frequency is determined based on the deviation between the actual arc therapy effect and the result specified in the therapy plan and the current pulse frequency.

In S103, the dose rate of the radiation beam emitted by the radiation source equipment is updated based on the output pulse frequency.

In the embodiments of the present disclosure, the dose rate of the radiation beam is updated based on actual irradiation of the tumor target region by adjusting the pulse frequency of the radiation beam emitted by the radiation source equipment to the output pulse frequency, and the tumor target region is irradiated by imposing, based on the updated dose rate, the radiation beam. As such, the radiation source equipment does not impose the radiation beam on the tumor target region at a fixed dose rate, and a flexibility of controlling dose rate of the radiation beam is great.

In some embodiments, in response to the above updated dose rate, the actually received dose of the radiation beam for the tumor target region approaches to the expected dose of the radiation beam for the tumor target region. In the embodiments of the present disclosure, the dose rate is dynamically updated, and the radiation beam is imposed to the tumor target region based on the new dose rate upon each update, such that a difference between the actual arc therapy effect and the result specified in the therapy plan is decreased, and the deviation is less, for example, the deviation is in a predetermined acceptable range. As such, the therapy effect on the tumor target region is improved.

Figure 2:
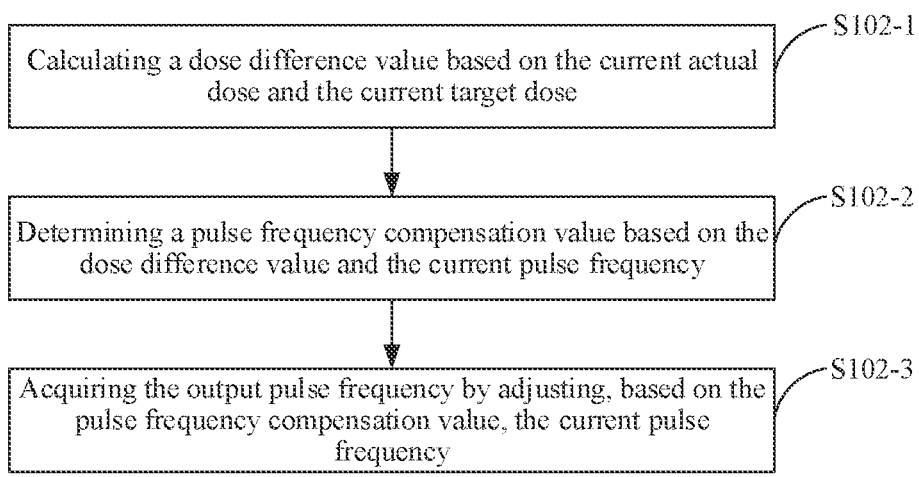
FIG. 2 is a flowchart of a method for determining an output pulse frequency according to some embodiments of the present disclosure.

On the basis of FIG. 1, an implementation of determining an output pulse frequency is provided in the embodiments of the present disclosure. Referring to FIG. 2, FIG. 2 is a flowchart of a method for determining an output pulse frequency according to some embodiments of the present disclosure. S102 includes sub-steps S102-1 to S102-3.

In S102-1, a dose difference value is calculated based on the current actual dose and the current target dose.

In the embodiments of the present disclosure, the dose difference value is an absolute value of the current actual dose minus the current target dose. A magnitude of the value is indicative of the deviation between the actual arc therapy effect and the result specified in the therapy plan.

In S102-2, a pulse frequency compensation value is determined based on the dose difference value and the current pulse frequency.

In the embodiments of the present disclosure, the pulse frequency compensation value is indicative of a change in pulse frequency according to which the radiation source equipment emits the radiation beam to ensure that the actual arc therapy effect does not deviate from the result specified in the therapy plan (for example, to ensure the current actual dose to approach to the current target dose, and a difference in dose is less). A magnitude of the pulse frequency compensation value is determined based on the dose difference value and the current pulse frequency.

In S102-3, the output pulse frequency is acquired by adjusting, based on the pulse frequency compensation value, the current pulse frequency.

In the embodiments of the present disclosure, the pulse frequency compensation value, the current pulse frequency, and the output pulse frequency meet a formula: $PRF_{set}=PRF_n-PRF_{Delta}$. $PRF_n$ represents the current pulse frequency, $PRF_{Delta}$ represents the pulse frequency compensation value, and $PRF_{set}$ represents the output pulse frequency. As the pulse frequency compensation value may be positive, negative, or zero, the output pulse frequency may be greater than, less than, or equal to the current pulse frequency.

In above embodiments of S102, the deviation between the actual arc therapy effect and the result specified in the therapy plan is represented by the dose difference value between the current actual dose and the current target dose. The pulse frequency compensation value is determined based on the dose difference value, and the output pulse frequency is acquired by adjusting, based on the pulse frequency compensation value, the current pulse frequency.

In some embodiments of S102, the deviation is represented by a ratio of the current actual dose to the current target dose, and the output pulse frequency is acquired by adjusting, based on the ratio, the current pulse frequency. The output pulse frequency is also determined in other optional manner, which is not limited in the embodiments of the present disclosure.

Figure 3:
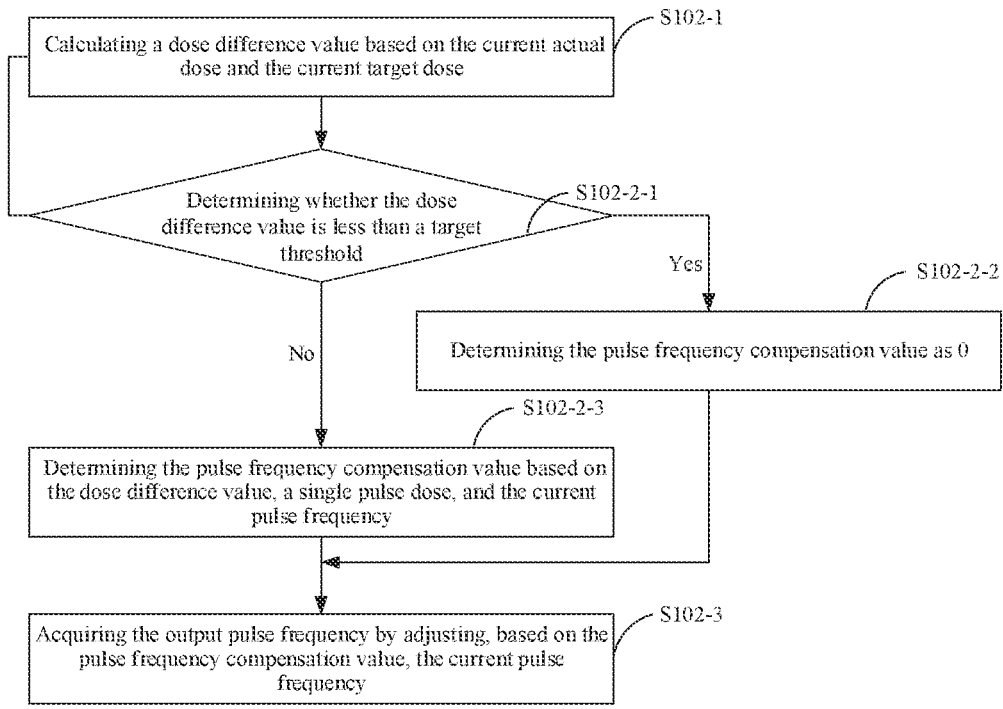
FIG. 3 is a flow chart of another method for determining an output pulse frequency according to some embodiments of the present disclosure.

On the basis of FIG. 2, an implementation of determining a pulse frequency compensation value is provided in the embodiments of the present disclosure. Referring to FIG. 3, FIG. 3 is a flowchart of another method for determining an output pulse frequency according to some embodiments of the present disclosure. The sub-step S102-2 includes sub-steps S102-2-1 to S102-2-3.

In S102-2-1, whether the dose difference value is less than a target threshold is determined.

In the embodiments of the present disclosure, the target threshold is an upper limit value of the dose difference value, and is indicative of an acceptable range of the deviation between the actual arc therapy effect and the result specified in the therapy plan. In the case that the dose difference value is less than the target threshold, S102-2-2 is performed. In the case that the dose difference value is not less than the target threshold, S102-2-3 is performed.

In S102-2-2, the pulse frequency compensation value is determined as 0 in response to the dose difference value being less than the target threshold.

In the embodiments of the present disclosure, in the case that the dose difference value is less than the target threshold, the deviation between the actual arc therapy effect and the result specified in the therapy plan is in the acceptable range. In this case, it is not necessary to update the dose rate of the radiation beam emitted by radiation source equipment, and thus the pulse frequency compensation value is determined as 0.

In S102-2-3, the pulse frequency compensation value is determined based on the dose difference value, a single pulse dose, and the current pulse frequency in response to the dose difference value being not less than the target threshold.

In the embodiments of the present disclosure, in the case that the dose difference value is not less than the target threshold, the deviation between the actual arc therapy effect and the result specified in the therapy plan is beyond the acceptable range. In this case, it is necessary to update the dose rate of the radiation beam emitted by radiation source equipment.

In above embodiments of S102-2, whether the deviation between the actual arc therapy effect and the result specified in the therapy plan is acceptable is determined by setting the target threshold for the dose difference value, and the pulse frequency compensation value is further determined in two manners.

In some embodiments of S102-2, three or more difference value ranges are set. Each difference value range corresponds to one method of determining the pulse frequency compensation value, and different methods of determining the pulse frequency compensation value are applied in response to the dose difference value being in different difference value ranges. For example, a determining method corresponding to a difference value range is to set the pulse frequency compensation value to a fixed value greater than 0. S102-2 is also implemented in other manners, which is not limited in the embodiments of the present disclosure.

In some embodiments, implementing processes of S102-2-3 are as follows.

In S102-2-3-1, a reference compensation value is determined based on the dose difference value, the single pulse dose, a first period, and a second period.

In the embodiments of the present disclosure, a time interval between each two adjacent executions of the method of adjusting the dose rates in the embodiments of the present disclosure is determined in conjunction with the first period and the second period. The first period is a duration required for each rotation of the radiation source equipment by an angle (for example, a target angle), and the second period is a number of rotations of the radiation source equipment between each two adjacent adjustments of the dose rate. For example, in the case that the radiation source equipment requires 10 ms for each rotation by 0.2°, and the radiation source equipment rotates 10 times between each two adjacent adjustments of the dose rate, 100 ms is required for the rotation by 2°, and thus the method for adjusting the dose rates in the embodiments of the present disclosure is performed each 100 ms.

In the embodiments of the present disclosure, the reference compensation value is positively correlated with the dose difference value, and is negatively correlated with the single pulse dose, the first period, and the second period. The dose difference value, the single pulse dose, the first period, the second period, and the reference compensation value meets the following formula:

$$\Delta PRF = \frac{\Delta IntegralDose}{DPP \cdot TaskCycle \cdot prfCatchCycle}.$$

$\Delta IntegralDose$ represents the dose difference value, DPP the single pulse dose with an unit of MU/pulse, TaskCycle represents the first period, prfCatchCycle represents the second period, and $\Delta PRF$ represents the reference compensation value.

In S102-2-3-2, a first correction coefficient is determined based on the dose difference value.

In the embodiments of the present disclosure, the first correction coefficient is positively correlated with the dose difference value. For example, the first correction coefficient is a value of a piecewise function of the dose difference value. The piecewise function is taken first parameters as a piecewise basis. The piecewise basis indicates parameters for defining different value ranges of independent variables in the piecewise function. The piecewise function is:

$$a = \begin{cases} R_1, 0 \le \Delta IntegralDose < D_1 \\ \frac{R_2 - R_1}{D_2 - D_1} \cdot (\Delta IntegralDose - D_1) + R_1, D_1 \le \Delta IntegralDose < D_2 \\ R_2, D_2 \le \Delta IntegralDose \end{cases}.$$

$\Delta IntegralDose$ represents the dose difference value, $D_1$, $D_2$, $R_1$, and $R_2$ represent the first parameters, and a represents the first correction coefficient.

Figure 4:
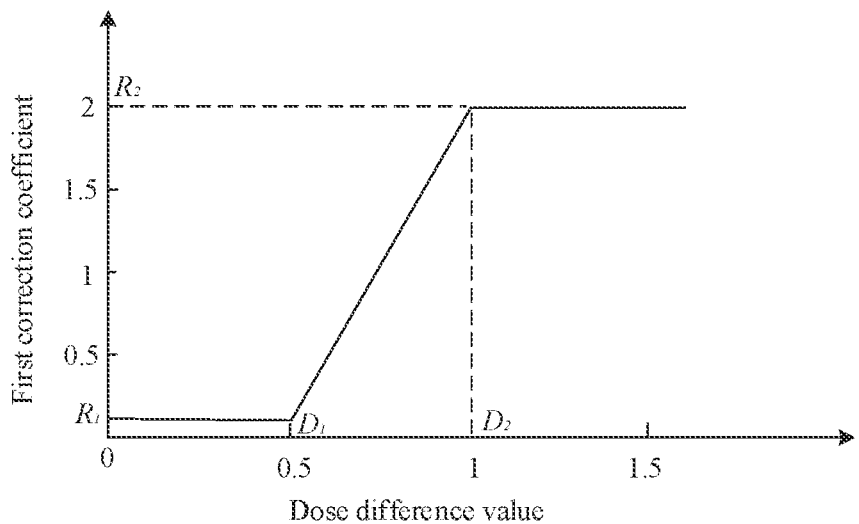
FIG. 4 is a schematic diagram of a function relationship of a first correction coefficient and a dose difference value according to some embodiments of the present disclosure.

In some embodiments, $D_1$, $D_2$, $R_1$, and $R_2$ are set as 0.5, 1, 0.1, and 2 respectively. In this case, a diagram of above piecewise function of the dose difference value is shown in FIG. 4. In the case that the dose difference value is less than 0.5, the first correction coefficient is 0.1. In the case that the dose difference value is greater than or equal to 1, the first correction coefficient is 2. In the case that the dose difference value is in a range of [0.5 to 1), the first correction coefficient is calculated based on the formula: 3.8× ($\Delta IntegralDose$–0.5)+0.1. That is, a value of the first correction coefficient is in a range of [0.1, 2].

In S102-2-3-3, a second correction coefficient is determined based on the reference compensation value.

In the embodiments of the present disclosure, the second correction coefficient is negatively correlated with the reference compensation value. The second correction coefficient is a value of a piecewise function of the reference compensation value, and the piecewise function is taken second parameters as a piecewise basis. The piecewise function is:

$$b = \begin{cases} Q_2, 0 \le \Delta PRF < P_1 \\ \frac{Q_1 - Q_2}{P_2 - P_1} (\Delta PRF - P_1) + Q_2, P_1 \le \Delta PRF < P_2 \\ Q_1, P_2 \le \Delta PRF \end{cases}.$$

$\Delta PRF$ represents the reference compensation value, $P_1$, $P_2$, $Q_1$, and $Q_2$ represent the second parameters, and b represents the second correction coefficient.

Figure 5:
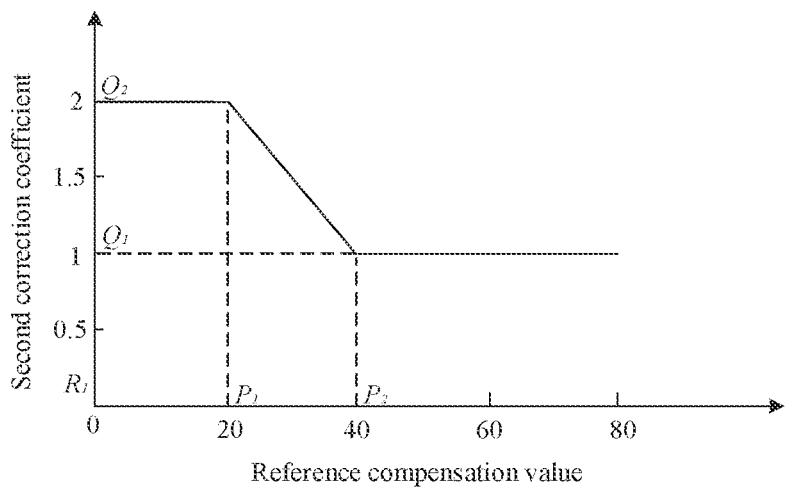
FIG. 5 is a schematic diagram of a function relationship of a second correction coefficient and a reference compensation value according to some embodiments of the present disclosure.

In some embodiments, $P_1$, $P_2$, $Q_1$, and $Q_2$ are set as 20, 40, 1, and 2 respectively. In this case, a diagram of above piecewise function of the reference compensation value is shown in FIG. 5. In the case that the reference compensation value is less than 20, the second correction coefficient is 2. In the case that the reference compensation value is greater than or equal to 40, the second correction coefficient is 1. In the case that the reference compensation value is in a range of [20, 40), the second correction coefficient is calculated based on the formula: −0.05×($\Delta PRF$−20)+2. That is, a value of the second correction coefficient is in a range of [1, 2].

In S102-2-3-4, the pulse frequency compensation value is determined based on the first correction coefficient, the second correction coefficient, the current pulse frequency, and the reference compensation value.

In the embodiments of the present disclosure, the pulse frequency compensation value is determined based on the first correction coefficient, the second correction coefficient, the current pulse frequency, and the reference compensation value to avoid the system oscillation caused by great pulse frequency compensation value, such that the determined pulse frequency compensation value is appropriate, and the system is stable.

In some embodiments of S102-2-3, the first correction coefficient, the second correction coefficient, and the reference compensation value are not calculated, a ratio of the dose difference value to the single pulse dose is calculated to determine the deviation of the number of the pulse, and the pulse frequency compensation value is determined based on the ratio and the current pulse frequency. S102-2-3 is also implemented in other manner, which is not limited in the embodiments of the present disclosure.

In some embodiments, implementing processes of S102-2-3-4 are as follows.

In S102-2-3-4a, a first threshold and a second threshold are determined based on the first correction coefficient, the second correction coefficient, and the current pulse frequency.

In S102-2-3-4b, the first threshold is determined as the pulse frequency compensation value in response to the reference compensation value being less than the first threshold.

In S102-2-3-4c, the reference compensation value is determined as the pulse frequency compensation value in response to the reference compensation value being greater than or equal to the first threshold and being less than or equal to the second threshold.

In S102-2-3-4d, the second threshold is determined as the pulse frequency compensation value in response to the reference compensation value being greater than the second threshold.

Above implementation processes meet the following formula:

$$PRF_{Delta} = \begin{cases} -a \times b \times PRF_n, \Delta PRF < -a \times b \times PRF_n \\ \Delta PRF, -a \times b \times PRF_n \le \Delta RPF \le a \times b \times PRF_n \\ a \times b \times PRF_n, \Delta RPF > a \times b \times PRF_n \end{cases}.$$

a represents the first correction coefficient, b represents the second correction coefficient, $PRF_n$ represents the current pulse frequency, $\Delta PRF$ represents the reference compensation value, $PRF_{Delta}$ represents the pulse frequency compensation value, $-a \times b \times PRF_n$ represents the first threshold, that is, a minimum value of the pulse frequency compensation value $PRF_{Delta}$, $a \times b \times PRF_n$ represents the second threshold, that is, a maximum value of the pulse frequency compensation value $PRF_{Delta}$.

In some embodiments of S102-2-4, the first threshold and the second threshold are not calculated, and a product of the first correction coefficient, the second correction coefficient, and the current pulse frequency is determined as the pulse frequency compensation value. S102-2-3-4 is also implemented in other manner, which is not limited in the embodiments of the present disclosure.

Figure 6:
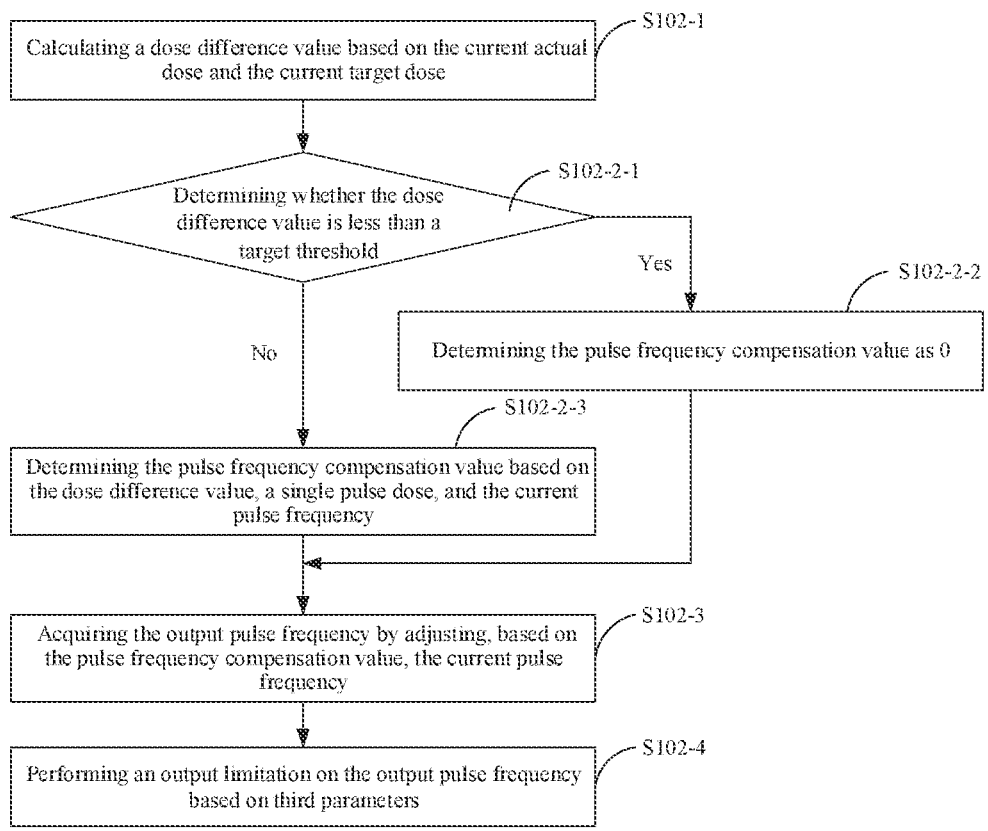
FIG. 6 is a flowchart of another method for determining an output pulse frequency according to some embodiments of the present disclosure.

On the basis of FIG. 2 and FIG. 3, another implementation of determining an output pulse frequency is provided in the embodiments of the present disclosure. Referring to FIG. 6, FIG. 6 is a flowchart of another method for determining an output pulse frequency according to some embodiments of the present disclosure. S102 includes sub-steps S102-4.

In S102-4, an output limitation is performed on the output pulse frequency based on third parameters.

In the embodiments of the present disclosure, the third parameters include a maximum dose rate of the radiation beam, a pulse frequency conversion coefficient, a pulse frequency tolerance value, and a maximum value of the output pulse frequency, and the third parameters are set by operators. The pulse frequency conversion coefficient is a parameter based on which a pulse frequency is converted to a rotation speed of the radiation source equipment. In the case that the pulse frequency is 600 Hz, the pulse frequency conversion coefficient is 3 (that is, the radiation source equipment emits three pulses each rotation), and an unit of the conversion coefficient is rotation/second (r/sec), a rotation speed of the radiation source equipment converted based on the pulse frequency is 600/3, that is, 200 r/sec. The pulse frequency tolerance value indicates an error value allowable by the pulse frequency of the radiation beam.

In the case that the radiation source equipment emits the radiation beam to irradiate the tumor target region, a magnitude of the output pulse frequency is limited based on the third parameters, such that a risk of damage on the organs around the tumor target region caused by great dose of the radiation beam is decreased, and the safety of the patient is ensured.

Implementing processes of S102-4 are as follows.

In S102-4-1, whether the output pulse frequency is greater than a ratio of the maximum dose rate of the radiation beam to the pulse frequency conversion coefficient is determined.

In the embodiments of the present disclosure, in the case that the output pulse frequency is less than or equal to the ratio of the maximum dose rate to the pulse frequency conversion coefficient, the dose rate of the radiation beam emitted by the radiation source equipment is updated based on the output pulse frequency. In the case that the output pulse frequency is greater than the ratio of the maximum dose rate to the pulse frequency conversion coefficient, S102-4-2 is performed.

In S102-4-2, a calculation result acquired based on the maximum dose rate, the pulse frequency conversion coefficient, the pulse frequency tolerance value, and the maximum value of the output pulse frequency is determined as the output pulse frequency in response to the output pulse frequency being greater than a ratio of the maximum dose rate to the pulse frequency conversion coefficient.

In the case that the output pulse frequency is greater than the ratio of the maximum dose rate to the pulse frequency conversion coefficient, the body of the patient is harmed where the dose rate of the radiation beam emitted by the radiation source equipment is updated based on the output pulse frequency. In the embodiments of the present disclosure, the output pulse frequency for updating the dose rate of the radiation beam emitted by the radiation source equipment is re-determined based on the maximum dose rate of the radiation beam, the pulse frequency conversion coefficient, the pulse frequency tolerance value, and the maximum value of the output pulse frequency using the following formula:

$$PRF_{set} = \min \frac{DoseRateMax}{PRFRatio} * (1 + PRFTolerace), PRFMax).$$

DoseRateMax represents the maximum dose rate, PRFRatio represents the pulse frequency conversion coefficient, PRFTolerace represents the pulse frequency tolerance value, PRFMax represents the maximum value of the output pulse frequency, and $PRF_{set}$ represents the output pulse frequency. The output pulse frequency determined based on the formula is a minimum between $$\frac{DoseRateMax}{PRFRatio} * (1 + PRFTolerace) \text{ and } PRFMax.$$

In implementing processes of S102-4, whether the output pulse frequency harms the safety of the patient is determined by determining whether the output pulse frequency is greater than a ratio of the maximum dose rate to the pulse frequency conversion coefficient. In addition, the output pulse frequency is re-updated in the case that the output pulse frequency harms the safety of the patient, such that the safety of the arc therapy process is improved.

Figure 7:
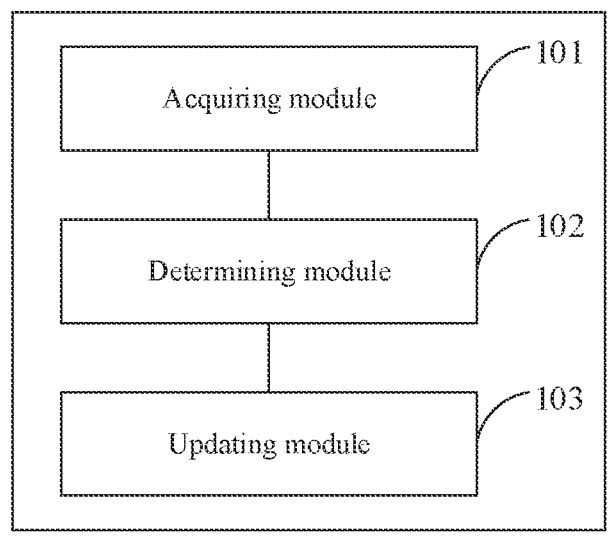
FIG. 7 is a schematic block diagram of an apparatus for adjusting dose rates according to some embodiments of the present disclosure.

For performing corresponding processes in above embodiments and some possible implementations, the following shows embodiments of an apparatus 100 for adjusting dose rates. Referring to FIG. 7, FIG. 7 is a schematic block diagram of an apparatus 100 for adjusting dose rates according to some embodiments of the present disclosure. It should be noted that the basic principles and technical effects of the apparatus 100 for adjusting the dose rates in the embodiments of the present disclosure are the same as those in above embodiments, and thus are not shown in the embodiments of the present disclosure for brief descriptions.

The apparatus 100 for adjusting the dose rates includes an acquiring module 101, a determining module 102, and an updating module 103.

The acquiring module 101 is configured to acquire a current actual dose, a current target dose, and a current pulse frequency, wherein the current pulse frequency is indicative of a dose rate of a radiation beam emitted by radiation source equipment, the current actual dose is an actually received dose of the radiation beam for a tumor target region, and the current target dose is an expected dose of the radiation beam for the tumor target region.

The determining module 102 is configured to determine an output pulse frequency based on the current actual dose, the current target dose, and the current pulse frequency.

The updating module 103 is configured to update, based on the output pulse frequency, the dose rate of the radiation beam emitted by the radiation source equipment.

In some embodiments, the determining module 102 is configured to: calculate a dose difference value based on the current actual dose and the current target dose, wherein the dose difference value is an absolute value of a difference value between the current actual dose and the current target dose; determine a pulse frequency compensation value based on the dose difference value and the current pulse frequency; and acquire the output pulse frequency by adjusting, based on the pulse frequency compensation value, the current pulse frequency.

In some embodiments, the determining module 102 is configured to: determine whether the dose difference value is less than a target threshold; determine the pulse frequency compensation value as 0 in response to the dose difference value being less than the target threshold; and determine, in response to the dose difference value being not less than the target threshold, the pulse frequency compensation value based on the dose difference value, a single pulse dose, and the current pulse frequency, wherein the single pulse dose is a dose of a signal pulse of the radiation beam emitted by the radiation source equipment.

In some embodiments, the determining module 102 is configured to:
- determine a reference compensation value based on the dose difference value, the single pulse dose, a first period, and a second period, wherein the reference compensation value is positively correlated with the dose difference value and is negatively correlated with the single pulse dose, the first period, and the second period, the first period is a duration required for each rotation of the radiation source equipment by a target angle, and the second period is a number of rotations of the radiation source equipment between each two adjacent adjustments of the dose rate;
- determine a first correction coefficient based on the dose difference value, wherein the first correction coefficient is a value of a piecewise function of the dose difference value, and is positively correlated with the dose difference value;
- determine a second correction coefficient based on the reference compensation value, wherein the second correction coefficient is a value of a piecewise function of the reference compensation value, and is negatively correlated with the reference compensation value; and
- determine the pulse frequency compensation value based on the first correction coefficient, the second correction coefficient, the current pulse frequency, and the reference compensation value.

In some embodiments, the determining module 102 is configured to:
- determine a first threshold and a second threshold based on the first correction coefficient, the second correction coefficient, and the current pulse frequency;
- determine the first threshold as the pulse frequency compensation value in response to the reference compensation value being less than the first threshold; determine the reference compensation value as the pulse frequency compensation value in response to the reference compensation value being greater than or equal to the first threshold and being less than or equal to the second threshold; and determine the second threshold as the pulse frequency compensation value in response to the reference compensation value being greater than the second threshold.

In some embodiments, the determining module 102 is configured to perform an output limitation on the output pulse frequency based on third parameters.

In some embodiments, the third parameters include a maximum dose rate of the radiation beam, a pulse frequency conversion coefficient, a pulse frequency tolerance value, and a maximum value of the output pulse frequency, and the pulse frequency conversion coefficient is a parameter based on which a pulse frequency is converted to a rotation speed of the radiation source equipment; and the determining module 102 is configured to: determine whether the output pulse frequency is greater than a ratio of the maximum dose rate to the pulse frequency conversion coefficient; and determine, in response to the output pulse frequency being greater than the ratio of the maximum dose rate to the pulse frequency conversion coefficient, a calculation result acquired based on the maximum dose rate of the radiation beam, the pulse frequency conversion coefficient, the pulse frequency tolerance value, and the maximum value of the output pulse frequency as the output pulse frequency.

In some embodiments, in response to the updated dose rate, the actually received dose of the radiation beam for the tumor target region approaches to the expected dose of the radiation beam for the tumor target region.

Figure 8:
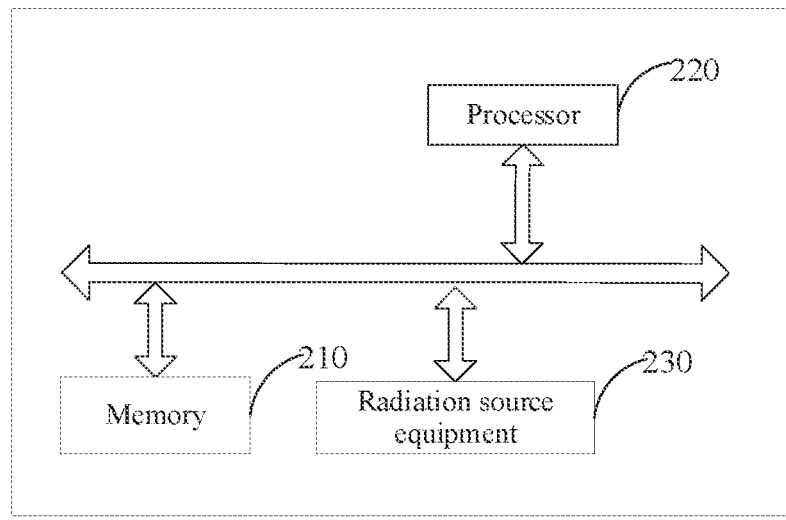
FIG. 8 is a schematic structural block diagram of a computer device according to some embodiments of the present disclosure.

Furthermore, referring to FIG. 8, FIG. 8 is a schematic structural block diagram of a computer device 200 according to some embodiments of the present disclosure. The computer device 200 includes a memory 210, a processor 220, and radiation source equipment 230.

The processor 220 is a general-purpose central processing unit (CPU), a microprocessor, an application-specific integrated circuit (ASIC), or one or more integrated circuits implemented by programs for controlling the method for adjusting the dose rates in the method embodiments.

The memory 210 is a read-only memory (ROM) or other types of static storage devices that can store static information and instructions, a random access memory (RAM) or other types of dynamic storage devices that can store information and instructions. The memory 210 can also be an electrically erasable programmable read-only memory (EEPROM), a compact disc read-only memory (CD-ROM) or other optical disc storage, optical disk storage (including compact disk, laser disk, optical disk, digital universal optical disk, blue-ray optical disk, and the like), disk storage media or other magnetic storage devices, or any other medium that can be used to carry (or store) the desired program codes in the form of instructions (or data structures) and can be accessed by the computer, but is not limited to this. The memory 210 can exist alone, and can be connected to the processor 220 via a communication bus. The memory 210 can also be integrated with the processor 220. The memory 210 is used to store the machine executable instructions executing the technical solutions in the present disclosure. The processor 220 is used to execute the machine executable instructions stored in the memory 210 to implement the above method embodiments.

The radiation source equipment 230 is an accelerator of a built-in multi-leaf collimator (MLC), a gate-controlled electron gun, or any device capable of emitting a radiation beam of changeable radiation field and dose rate, but is not limited to this. The radiation source equipment 230 is connected to the processor 220 via a communication bus. The processor 220, when loading and executing the machine executable instructions stored in the memory 210, causes the radiation source equipment 230 to implement the above method embodiments.

As the computer device 200 in the embodiments of the present disclosure is another implementation of the method for adjusting the dose rates in above embodiments, the acquired technical effects can be referred to above embodiments, which are not repeated herein.

A readable storage medium storing computer executable instructions is further provided in the embodiments of the present disclosure. The computer executable instructions, when loaded and run, cause the processor to perform related processes of the method for adjusting the dose rates in above method embodiments.

In summary, in the method and apparatus for adjusting the dose rates, the computer device, and the storage medium, a current actual dose, a current target dose, and a current pulse frequency are first acquired, and the current pulse frequency is indicative of a dose rate of a radiation beam emitted by radiation source equipment. Then, an output pulse frequency is determined based on the current actual dose, the current target dose, and the current pulse frequency, and the dose rate of the radiation beam emitted by the radiation source equipment is updated based on the output pulse frequency. The radiation source equipment does not impose the radiation beam to the tumor target region at a fixed dose rate, and thus a flexibility of controlling the dose rate of the radiation beam is great.

In addition, in response to the updated dose rate, the actually received dose of the radiation beam for the tumor target region approaches to the expected dose of the radiation beam for the tumor target region. As such, the deviation between the actual arc therapy effect and the result specified in the therapy plan is less, and thus the therapy effect on the tumor target region is improved.

It should be noted that the device in the above embodiments is only illustrated by the division of the above functional modules. In some embodiments, the above functions can be achieved by different functional modules as required, that is, the internal structure of the device can be divided into different functional modules to achieve all or part of above functions.

Described above are only optional embodiments of the present disclosure, but the scope of protection of the present disclosure is not limited to this. Any easily considered changes or substitutes, made within the technical scope of the present disclosure by those skilled in the art, shall fall within the scope of protection of the present disclosure. Therefore, the scope of protection of the present disclosure shall be the scope of the claims.

What is claimed:

1. A method for adjusting dose rates, comprising:
    acquiring a current actual dose, a current target dose, and a current pulse frequency, wherein the current pulse frequency is indicative of a dose rate of a radiation beam emitted by radiation source equipment, the current actual dose is an actually received dose of the radiation beam for a tumor target region, and the current target dose is an expected dose of the radiation beam for the tumor target region;
    calculating a dose difference value based on the current actual dose and the current target dose, wherein the dose difference value is an absolute value of a difference value between the current actual dose and the current target dose;
    determining, in response to the dose difference value being not less than a target threshold, a reference compensation value based on the dose difference value, a single pulse dose, a first period, and a second period, wherein the reference compensation value is positively correlated with the dose difference value and is negatively correlated with the single pulse dose, the first period, and the second period, the single pulse dose is a dose of a signal pulse of the radiation beam emitted by the radiation source equipment, the first period is a duration required for each rotation of the radiation source equipment by a target angle, and the second period is a number of rotations of the radiation source equipment between each two adjacent adjustments of the dose rate;
    determining a first correction coefficient based on the dose difference value, wherein the first correction coefficient is a value of a piecewise function of the dose difference value and is positively correlated with the dose difference value;
    determining a second correction coefficient based on the reference compensation value, wherein the second correction coefficient is a value of a piecewise function of the reference compensation value and is negatively correlated with the reference compensation value;
    determining a pulse frequency compensation value based on the first correction coefficient, the second correction coefficient, the current pulse frequency, and the reference compensation value;
    acquiring an output pulse frequency by adjusting, based on the pulse frequency compensation value, the current pulse frequency; and
    updating, based on the output pulse frequency, the dose rate of the radiation beam emitted by the radiation source equipment.

2. The method according to claim 1, wherein determining the pulse frequency compensation value based on the first correction coefficient, the second correction coefficient, the current pulse frequency, and the reference compensation value comprises:
    determining a first threshold and a second threshold based on the first correction coefficient, the second correction coefficient, and the current pulse frequency;
    determining the first threshold as the pulse frequency compensation value in response to the reference compensation value being less than the first threshold;
    determining the reference compensation value as the pulse frequency compensation value in response to the reference compensation value being greater than or equal to the first threshold and being less than or equal to the second threshold; and
    determining the second threshold as the pulse frequency compensation value in response to the reference compensation value being greater than the second threshold.

3. A method for adjusting dose rates, comprising:
    acquiring a current actual dose, a current target dose, and a current pulse frequency, wherein the current pulse frequency is indicative of a dose rate of a radiation beam emitted by radiation source equipment, the current actual dose is an actually received dose of the radiation beam for a tumor target region, and the current target dose is an expected dose of the radiation beam for the tumor target region;
    calculating a dose difference value based on the current actual dose and the current target dose, wherein the dose difference value is an absolute value of a difference value between the current actual dose and the current target dose;
    determining a pulse frequency compensation value based on the dose difference value and the current pulse frequency;

acquiring an output pulse frequency by adjusting, based on the pulse frequency compensation value, the current pulse frequency;

updating, based on the output pulse frequency, the dose rate of the radiation beam emitted by the radiation source equipment; and performing an output limitation on the output pulse frequency based on third parameters, wherein the third parameters comprise a maximum dose rate of the radiation beam, a pulse frequency conversion coefficient, a pulse frequency tolerance value, and a maximum value of the output pulse frequency, and the pulse frequency conversion coefficient is a parameter based on which a pulse frequency is converted to a rotation speed of the radiation source equipment;

wherein performing the output limitation on the output pulse frequency based on the third parameters comprises:

determining, in response to the output pulse frequency being greater than a ratio of the maximum dose rate to the pulse frequency conversion coefficient, a calculation result acquired based on the maximum dose rate of the radiation beam, the pulse frequency conversion coefficient, the pulse frequency tolerance value, and the maximum value of the output pulse frequency as the output pulse frequency.

4. The method according to claim 1, wherein in response to the updated dose rate, the actually received dose of the radiation beam for the tumor target region approaches to the expected dose of the radiation beam for the tumor target region.

5. A computer device, comprising: a memory, a processor, and radiation source equipment, wherein the memory is configured to store one or more computer programs, and the processor, when loading and running the one or more computer programs, is caused to perform the method as defined in claim 1.

6. A non-transitory computer-readable storage medium, storing one or more computer programs thereon, wherein the one or more computer programs, when loaded and run by a processor, cause the processor to perform the method as defined in claim 1.

7. A computer program product, comprising instructions, wherein the computer program product, when loaded and run by a computer, causes the computer to perform the method as defined in claim 1.

8. A chip, comprising: at least one of a programmable logic circuit and a program instruction, wherein the chip, when running, is caused to perform the method as defined in claim 1.

9. The method according to claim 3, wherein in response to the updated dose rate, the actually received dose of the radiation beam for the tumor target region approaches the expected dose of the radiation beam for the tumor target region.

10. A computer device, comprising: a memory, a processor, and radiation source equipment, wherein the memory is configured to store one or more computer programs, and the processor, when loading and running the one or more computer programs, is caused to perform the method as defined in claim 3.

11. A non-transitory computer-readable storage medium, storing one or more computer programs thereon, wherein the one or more computer programs, when loaded and run by a processor, cause the processor to perform the method as defined in claim 3.

12. A computer program product, comprising instructions, wherein the computer program product, when loaded and run by a computer, causes the computer to perform the method as defined in claim 3.

13. A chip, comprising: at least one of a programmable logic circuit and a program instruction, wherein the chip, when running, is caused to perform the method as defined in claim 3.

* * * * *